US009683976B2

(12) United States Patent
Mann et al.

(10) Patent No.: US 9,683,976 B2
(45) Date of Patent: Jun. 20, 2017

(54) CONTAINERS AND SYSTEMS FOR THE MEASUREMENT OF RADIOACTIVE GASES AND RELATED METHODS

(71) Applicant: BATTELLE ENERGY ALLIANCE, LLC., Idaho Falls, ID (US)

(72) Inventors: Nicholas R Mann, Idaho Falls, ID (US); Matthew G Watrous, Idaho Falls, ID (US); Christopher P Oertel, Idaho Falls, ID (US); Christopher A McGrath, Blackfoot, ID (US)

(73) Assignee: BATTELLE ENERGY ALLIANCE, LLC., Idaho Falls, ID (US)

(*) Notice: Subject to any disclaimer, the term of this patent is extended or adjusted under 35 U.S.C. 154(b) by 72 days.

(21) Appl. No.: 14/826,056

(22) Filed: Aug. 13, 2015

(65) Prior Publication Data
US 2016/0047785 A1  Feb. 18, 2016

Related U.S. Application Data

(60) Provisional application No. 62/038,040, filed on Aug. 15, 2014.

(51) Int. Cl.
*G01N 33/00* (2006.01)
*G01T 7/02* (2006.01)

(52) U.S. Cl.
CPC .......... *G01N 33/0055* (2013.01); *G01T 7/02* (2013.01)

(58) Field of Classification Search
CPC .......... G01N 33/0055; G01N 33/0009; G01N 33/0011; G01N 33/0004; G01N 33/0036; G01N 2033/0019; G01N 1/2273; G01T 7/02

USPC .............................................. 73/31.01, 31.02
See application file for complete search history.

(56) References Cited

U.S. PATENT DOCUMENTS

| | | | |
|---|---|---|---|
| 6,184,531 B1* | 2/2001 | Smart | G01T 1/178 250/253 |
| 7,202,478 B2* | 4/2007 | Ramsden | G01T 1/20 250/361 R |
| 7,566,881 B2* | 7/2009 | Parvin | G01S 7/4802 250/394 |

(Continued)

OTHER PUBLICATIONS

Bowyer et al., "Automatic Radioxenon Analyzer for CTBT Monitoring," Report Prepared for the U.S. Department of Energy, PNNL-11424, UC-713, Nov. 1996, 47 pages.

*Primary Examiner* — Peter Macchiarolo
*Assistant Examiner* — Nathaniel Kolb
(74) *Attorney, Agent, or Firm* — TraskBritt

(57) ABSTRACT

Containers for a fluid sample containing a radionuclide for measurement of radiation from the radionuclide include an outer shell having one or more ports between an interior and an exterior of the outer shell, and an inner shell secured to the outer shell. The inner shell includes a detector receptacle sized for at least partial insertion into the outer shell. The inner shell and outer shell together at least partially define a fluid sample space. The outer shell and inner shell are configured for maintaining an operating pressure within the fluid sample space of at least about 1000 psi. Systems for measuring radioactivity in a fluid include such a container and a radiation detector received at least partially within the detector receptacle. Methods of measuring radioactivity in a fluid sample include maintaining a pressure of a fluid sample within a Marinelli-type container at least at about 1000 psi.

21 Claims, 4 Drawing Sheets

(56) References Cited

U.S. PATENT DOCUMENTS

2010/0084561 A1\* 4/2010 Tranter .................. G01T 1/203
250/363.01

\* cited by examiner

CONTAINERS AND SYSTEMS FOR THE MEASUREMENT OF RADIOACTIVE GASES AND RELATED METHODS

CROSS-REFERENCE TO RELATED APPLICATION

This application claims the benefit of the filing date of the U.S. Provisional Patent Application No. 62/038,040, filed Aug. 15, 2014, the disclosure of which is hereby incorporated herein in its entirety by this reference.

GOVERNMENT RIGHTS

This invention was made with government support under Contract Number DE-AC07-05ID14517 awarded by the United States Department of Energy. The government has certain rights in the invention.

FIELD

Embodiments of the present disclosure relate to devices for the measurement of radioactive gases, such as ambient air including radioactive isotopes, and related methods.

BACKGROUND

The international Comprehensive Nuclear-Test-Ban Treaty (CTBT) includes a verification regime to detect any nuclear explosion in the world. Part of the verification regime includes the monitoring and detection of radionuclides in the atmosphere. Radionuclides of interest include radioactive isotopes of the noble gas xenon (e.g., $^{135}$Xe, $^{133}$Xe, $^{133m}$Xe, and $^{131m}$Xe). Noble gas collection and radionuclide measurement systems include radiation detectors that require calibration to verify the systems are working properly and providing accurate quantitative results. Calibration includes exposing the systems to gas samples that include a known content of a radionuclide of interest. Standard gas samples used for calibration include radioxenon (i.e., radioactive isotopes of xenon) mixed with stable xenon (i.e., non-radioactive isotopes of xenon) or radioxenon mixed with air (for example, approximately 87 ppb radioxenon in air). Measuring radioxenon in stable xenon involves a small volume of gas with a relatively easily detectable radioactive signal. However, the detection of radionuclides in the atmosphere for the CTBT or for other purposes involves the detection of radionuclides in ambient air, hereinafter referred to as "air" for convenience.

Measuring radioxenon in air involves a large volume of gas with a relatively small radioactive signal due to the low concentration of radioxenon. Accurate calibration and direct measurement of radioxenon in air is difficult based on several factors. First, radioxenon isotopes have a short half-life, which makes detecting radioxenon over a long period of time difficult, if not impossible. Second, large-volume, low-pressure samples include outer portions of the samples that are far from the radiation detector, resulting in low measurement efficiency. Third, although small-volume, high-pressure samples provide a more concentrated and higher signal for measuring, such samples require thick-walled containers to attain and maintain a high pressure. The thick walls attenuate (i.e., block) measurable gamma signals emitted from the radioxenon. While extraction of radioxenon from air for measurement is possible, it remains difficult to accurately quantify the amount of air processed and separated from the extracted radioxenon. Thus, it is difficult to accurately estimate the radioxenon concentration in the original sample.

The measurable intensity of gamma signals from a sample of radioxenon (or other radionuclides) in air is reduced by attenuation from the air itself and from any barrier between the sample and the radiation detector. Attenuation is a function of a distance that the gamma signals travel from the sample to the radiation detector in addition to any barrier that the gamma signal must pass through. Some existing radionuclide measurement systems include gas containers (e.g., Marinelli-type containers) having sidewalls fabricated from thin plastic to reduce attenuation. Marinelli-type containers generally include an outer shell, an inner shell for receipt of a radiation detector, and a space between the outer shell and inner shell for containing a sample fluid. However, such existing plastic, gas containers for detection of radionuclides have a relatively low maximum operating pressure (e.g., 10 psi) and are generally not capable of use for detection of low activity, low energy, and high pressure gases, such as radioxenon in compressed air.

BRIEF SUMMARY

In some embodiments, the present disclosure includes containers for a fluid sample containing a radionuclide for measurement of radiation from the radionuclide. Such containers include an outer shell and an inner shell secured to the outer shell. The outer shell includes one or more ports extending between an interior and an exterior of the outer shell. The inner shell includes a detector receptacle sized for at least partial insertion into the interior of the outer shell. The inner shell and the outer shell together at least partially define a fluid sample space proximate the detector receptacle. The outer shell and the inner shell are each configured for maintaining an operating pressure within the fluid sample space of at least about 1000 psi. In some embodiments, the present disclosure also includes a system for measuring radioactivity in a fluid including such a container and a radiation detector received at least partially within an interior of the detector receptacle.

In some embodiments, the present disclosure includes methods of measuring radioactivity in a fluid sample. In accordance with such methods, a fluid sample is introduced into a Marinelli-type container. A pressure of the fluid sample is maintained within the Marinelli-type container at least at about 1000 psi. A radiation detector is positioned within an inner shell of the Marinelli-type container, and a gamma signal from the fluid sample within the Marinelli-type container is measured.

DETAILED DESCRIPTION

Figure 2:
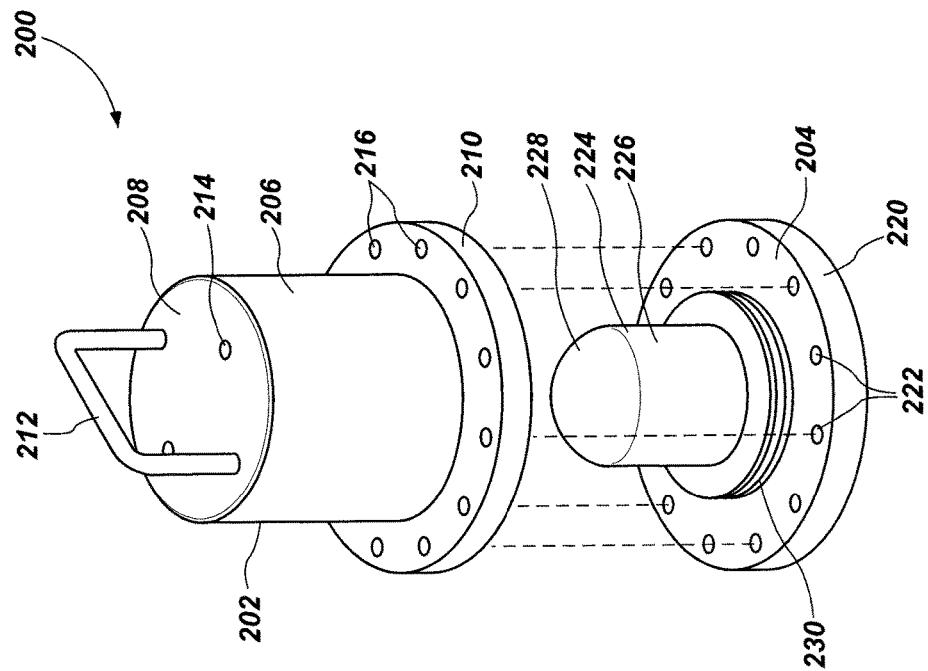
FIG. 2 shows an exploded perspective view of a Marinelli-type container for measuring radioactivity in a fluid sample, according to another embodiment of the present disclosure.

The following description provides specific details, such as material types, material thicknesses, and processing conditions in order to provide a thorough description of embodiments of the present disclosure. However, a person of ordinary skill in the art will understand that the embodiments of the present disclosure may be practiced without employing these specific details. Indeed, the embodiments of the present disclosure may be practiced in conjunction with conventional fabrication techniques and materials employed in the industry.

In the following detailed description, reference is made to the accompanying drawings, which form a part hereof, and in which is shown, by way of illustration, specific embodiments in which the present disclosure may be practiced. These embodiments are described in sufficient detail to enable a person of ordinary skill in the art to practice the present disclosure. However, other embodiments may be utilized, and structural and compositional changes may be made without departing from the scope of the disclosure. The illustrations presented herein are not meant to be actual views of any particular system, device, structure, or process, but are idealized representations which are employed to describe embodiments of the present disclosure. The drawings presented herein are not necessarily drawn to scale.

As used herein, the term "substantially" in reference to a given parameter, property, or condition means and includes to a degree that one skilled in the art would understand that the given parameter, property, or condition is met with a small degree of variance, such as within acceptable manufacturing tolerances. For example, a parameter that is substantially met may be at least about 90% met, at least about 95% met, or even at least about 99% met.

As used herein, any relational term, such as "first," "second," etc., is used for clarity and convenience in understanding the disclosure and accompanying drawings and does not connote or depend on any specific preference, orientation, or order, except where the context clearly indicates otherwise.

The embodiments of the present disclosure include devices for the measurement of radioactive gases. The devices may include a Marinelli-type container having an inner shell configured for receiving a radiation detector (e.g., a high purity gel (HPGe) detector) therein and an outer shell, with a space between the inner shell and the outer shell for housing a fluid sample. Materials of the outer shell and inner shell may be sufficiently thick and rigid to hold a fluid pressure within the space of at least about 1000 psi, such as at least about 5000 psi. The material of the inner shell may be selected and may have a shape and thickness to allow gamma radiation to pass therethrough from within the space to a detector positioned in the inner shell. By way of example and not limitation, the material of the inner shell may comprise an aluminum material or a carbon composite material (e.g., a carbon fiber in a matrix of an epoxy, cyanate ester and/or benzoxazine material, such as materials commercially available from Composite Technology Development, Inc. of Lafayette, Colo.). The shape of the inner shell may include, for example, a cylindrical tube with a substantially flat end or a cylindrical tube with a rounded (e.g., hemispherical) end.

Figure 1:
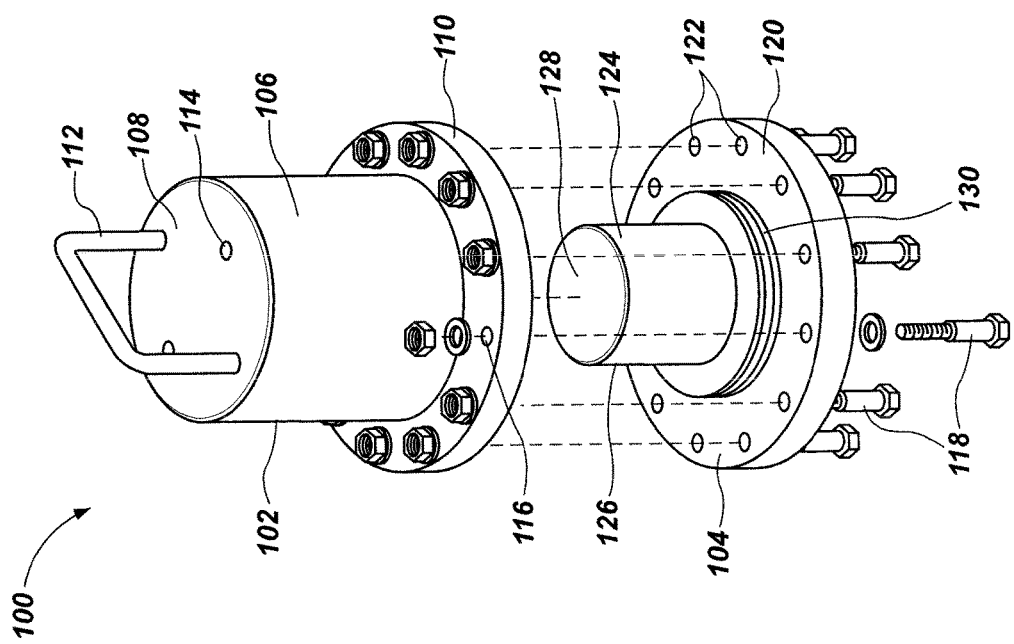
FIG. 1 shows an exploded perspective view of a Marinelli-type container for measuring radioactivity in a fluid sample, according to an embodiment of the present disclosure.

Referring to FIG. 1, a first embodiment of a Marinelli-type container 100 includes an outer shell 102 and an inner shell 104 configured and sized to fit at least partially within the outer shell 102. The outer shell 102 may include a cylindrical outer wall portion 106, an end plate portion 108, and a flange 110. Optionally, a handle 112 may be attached (e.g., screwed and/or welded, depending on materials employed) to the end plate portion 108. One or more ports 114 may extend through the end plate portion 108 for introducing a fluid (e.g., a compressed gas sample, ambient air) into or removing a fluid (e.g., a compressed gas sample, ambient air) out of an interior of the outer shell 102. The flange 110 may be at an end of the cylindrical outer wall portion 106 opposite the end plate portion 108. The flange 110 may include holes 116 sized and configured to receive bolts 118 therethrough for coupling (e.g., securing) the outer shell 102 to the inner shell 104. The outer shell 102 may be formed of any non-reactive material at any thickness that is sufficient to hold a sample fluid (e.g., a compressed gas sample) therein at an operating pressure (e.g., at least about 1000 psi, at least about 3000 psi, or at least about 5000 psi). For example, the outer shell 102 may be formed of a stainless steel material, an aluminum material, or a carbon composite material. Other features and characteristics of the outer shell 102 are described below with reference to FIG. 5.

The inner shell 104 may include a flange 120 that includes holes 122 sized and configured to receive the bolts 118 therethrough for coupling (e.g., securing) the inner shell 104 to the outer shell 102. The inner shell 104 may include a detector receptacle 124 sized and configured to be inserted into the interior of the outer shell 102 when the inner shell 104 is operably coupled to the outer shell 102 with the bolts 118. The detector receptacle 124 may include a cylindrical inner wall portion 126 and an end plate portion 128 at an opposite end of the cylindrical inner wall portion 126 from the flange 120. The cylindrical inner wall portion 126 of the detector receptacle 124 may be a hollow tube sized and configured for receipt of a radiation detector, such as an HPGe detector. In the first embodiment of the Marinelli-type container 100, the end plate portion 128 of the inner shell 104 is substantially flat, as shown in FIG. 1. Thus, the inner shell 104 is also referred to herein as a flat inner shell 104, and the first embodiment of the Marinelli-type container 100 is also referred to herein as a flat Marinelli-type container 100. An O-ring 130 or other sealing element may be included in the flat Marinelli-type container 100 to provide a fluid-tight seal between the inner shell 104 and outer shell 102 when operably coupled together.

The inner shell 104 may be formed of a non-reactive material at a thickness that is sufficient to hold a fluid sample (e.g., a compressed gas sample) within the flat Marinelli-type container 100 at an operating pressure (e.g., at least about 1000 psi, at least about 3000 psi, or at least about 5000 psi), while reducing attenuation of a gamma signal from a fluid sample including radionuclides. By way of example and not limitation, a material suitable for the inner shell 104 may be an aluminum material or a carbon composite material. Other features and characteristics of the flat inner shell 104 are described below with reference to FIG. 3.

In some embodiments, the outer shell 102 and inner shell 104 may be configured for coupling to each other in a manner that does not use the bolts 118 and holes 116, 122 in the respective flanges 110, 120. For example, the outer shell 102 and inner shell 104 may be configured for coupling via a weld or an adhesive, in which case the O-ring 130 may be omitted. By way of another example, the outer shell 102 and the inner shell 104 may include one or more sets of threads for screwing the outer shell 102 directly onto the inner shell 104, in which case the O-ring 130 may or may not be included. By way of a further example, clamps may be used to secure the outer shell 102 to the inner shell 104 by the flanges 110 and 120. Thus, any combination of welding, adhesion, clamps, screwing via threads, an O-ring 130, and bolts 118 and holes 116, 122 may be used to couple the outer shell 102 to the inner shell 104 in a manner sufficient to form a fluid-tight seal between the outer shell 102 and the inner shell 104 when a pressurized fluid sample is within the Marinelli-type container 100.

Referring to FIG. 2, a second embodiment of a Marinelli-type container 200 includes an outer shell 202 and an inner shell 204 configured to fit at least partially within the outer shell 202. The outer shell 202 may be substantially the same (e.g., identical) as the outer shell 102 described above with reference to FIG. 1. Thus, the outer shell 202 may also include a cylindrical outer wall portion 206, an end plate portion 208 with one or more ports 214 extending therethrough, optionally a handle 212 attached to the end plate portion 208, and a flange 210. Holes 216 may be included in the flange 210 and may be sized and configured to receive bolts therethrough for coupling (e.g., securing) the outer shell 202 to the inner shell 204. An O-ring 230 may be included for providing a fluid-tight seal when the outer shell 202 is coupled to the inner shell 204.

The inner shell 204 of the second embodiment of the Marinelli-type container 200 may be similar to the inner shell 104 described above with reference to FIG. 1, in that the inner shell 204 includes a flange 220 with holes 222 sized and configured to receive bolts therethrough for coupling (e.g., securing) the inner shell 204 to the outer shell 202. The inner shell 204 may also include a detector receptacle 224 including a cylindrical inner wall portion 226 and an end plate portion 228. However, rather than being substantially flat as is the end plate portion 128 described with reference to FIG. 1, the end plate portion 228 shown in FIG. 2 may be round (e.g., hemispherical). Thus, the inner shell 204 may also be referred to herein as the round inner shell 204 and the second embodiment of the Marinelli-type container 200 may be referred to herein as the round Marinelli-type container 200. A rounded shape of the end plate portion 228 may allow for added strength with a reduced wall thickness for decreased gamma signal attenuation, as discussed below. Other features and characteristics of the round inner shell 204 are described below with reference to FIG. 4.

Figure 3:
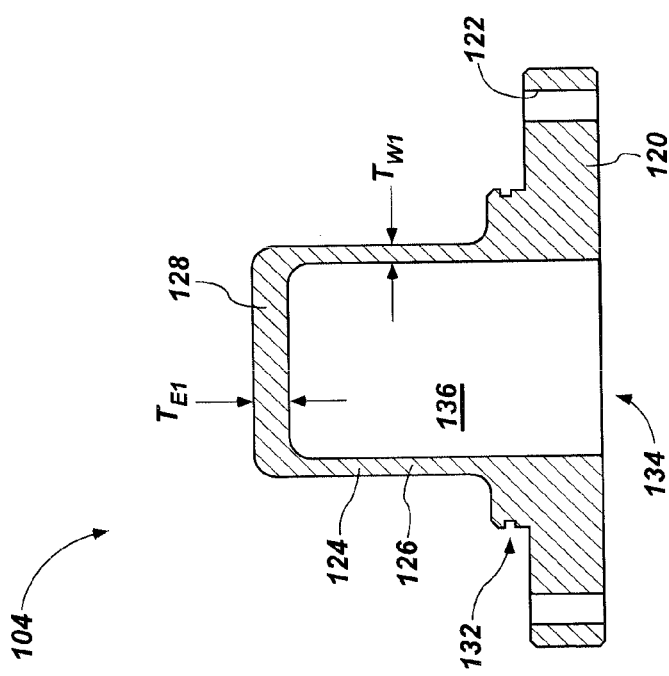
FIG. 3 shows a detailed cross-sectional view of a flat inner shell of the Marinelli-type container of FIG. 1.

FIG. 3 shows a detailed cross-sectional view of the flat inner shell 104 of FIG. 1. As shown in FIG. 3, the flat inner shell 104 may include an annular groove 132 sized and configured for receipt of an O-ring (e.g., the O-ring 130 shown in FIG. 1). The detector receptacle 124 may include an opening 134 into an interior 136 of the detector receptacle 124. The interior 136 of the detector receptacle 124 may be defined as a space within and between the cylindrical inner wall portion 126 and the end plate portion 128. The opening 134 may pass through the flange 120 from an end of the detector receptacle 124 opposite the end plate portion 128. The opening 134 may be sufficiently large to enable a radiation detector to be received at least partially within the interior 136 of the detector receptacle 124 when in use.

The material and thickness of the detector receptacle 124 may be selected by one of ordinary skill in the art after balancing considerations of, for example, lack of reactivity with a fluid sample to be measured, sufficient structural integrity under operating pressures, and reduction of attenuation of a gamma signal from the fluid sample to be measured. As discussed above, material of the detector receptacle 124 may be, for example, an aluminum material or a carbon composite material. An end plate thickness $T_{E1}$ of the end plate portion 128 of the flat inner shell 104 and a wall thickness $T_{W1}$ of the cylindrical inner wall portion 126 of the flat inner shell 104 may be selected to withstand operating fluid pressures while reducing attenuation of a gamma signal through the detector receptacle 124 and into the interior 136 of the detector receptacle 124. To withstand a given pressure, cylindrical pressure vessels with substantially flat end caps require a relatively greater thickness of the substantially flat end caps compared to cylindrical side walls thereof. Thus, in some embodiments, the end plate thickness $T_{E1}$ of the end plate portion 128 may be relatively thicker than the wall thickness $T_{W1}$ to withstand the operating fluid pressures (e.g., at least about 1000 psi, at least about 3000 psi, at least about 5000 psi). Conversely, the wall thickness $T_{W1}$ may be relatively thinner than the end plate thickness $T_{E1}$ to reduce attenuation through the cylindrical inner wall portion 126. By way of example and not limitation, in an embodiment in which aluminum is used for the flat inner shell 104, the end plate thickness $T_{E1}$ may be between about 0.5 inch and about 1.0 inch, such as about 0.6 inch, and the wall thickness $T_{W1}$ may be between about 0.25 inch and about 0.5 inch, such as about 0.3 inch. The actual thicknesses $T_{E1}$ and $T_{W1}$ for a given embodiment may depend on various factors, such as the particular material selected for the flat inner shell 104, the overall size of the flat inner shell 104, target operating pressures, and safety factors.

Figure 4:
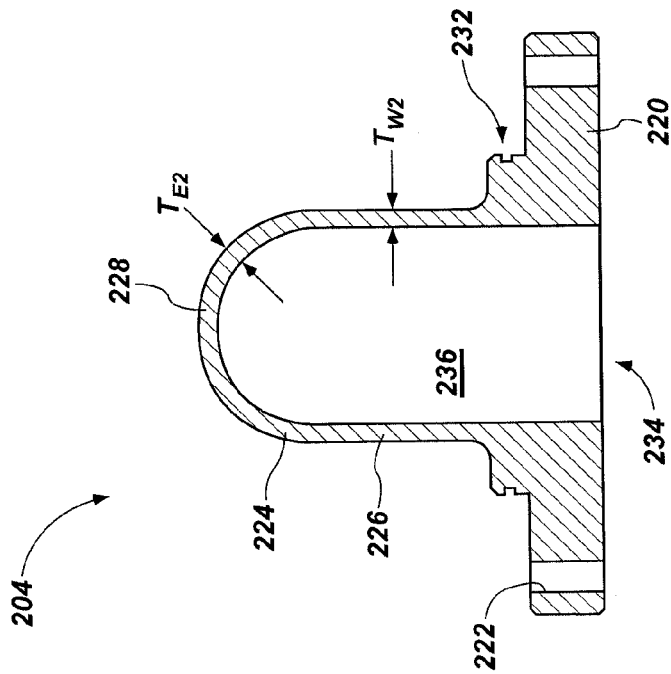
FIG. 4 shows a detailed cross-sectional view of a round inner shell of the Marinelli-type container of FIG. 2.

FIG. 4 shows a detailed cross-sectional view of the round inner shell 204 of FIG. 2. As shown in FIG. 4, the round inner shell 204 may include an annular groove 232 sized and configured for receipt of a high-pressure seal (e.g., the O-ring 230 shown in FIG. 2). The detector receptacle 224 may include an opening 234 into an interior 236 of the detector receptacle 224. The interior 236 of the detector receptacle 224 may be defined as a space within and between the cylindrical inner wall portion 226 and the end plate portion 228. The opening 234 may pass through the flange 220 from an end of the detector receptacle 224 opposite the end plate portion 228. The opening 234 may be sufficiently large to enable a radiation detector to be inserted and positioned at least partially within the interior 236 of the detector receptacle 224 when in use.

The material and thickness of the detector receptacle 224 may be selected by one skilled in the art after balancing considerations of, for example, lack of reactivity with a fluid sample to be measured, sufficient structural integrity under operating pressures, and reduction of attenuation of a gamma signal from the fluid sample to be measured. Material of the detector receptacle 224 may be, for example, an aluminum material or a carbon composite material. An end plate thickness $T_{E2}$ of the end plate portion 228 of the round inner shell 204 and a wall thickness $T_{W2}$ of the cylindrical inner wall portion 226 of the round inner shell 204 may be selected to withstand operating fluid pressures while reducing attenuation of a gamma signal through the detector receptacle 224 and into the interior 236 of the detector receptacle 224. To withstand a given pressure, cylindrical pressure vessels with round (e.g., hemispherical) end caps may have a substantially constant thickness of both the round end caps and the cylindrical side walls thereof. Thus, in some embodiments, an end plate thickness $T_{E2}$ of the end plate portion 228 that is substantially the same as the wall thickness $T_{W2}$ may withstand the operating fluid pressures (e.g., at least about 1000 psi, at least about 3000 psi, at least about 5000 psi). By way of example and not limitation, in an embodiment in which aluminum is used for the round inner shell 204, the end plate thickness $T_{E2}$ and the wall thickness $T_{W2}$ may each be between about 0.25 inch and about 0.5 inch, such as about 0.3 inch. The actual thicknesses $T_{E2}$ and $T_{W2}$ may depend on various factors, such as the particular material selected for the round inner shell 204, the overall size of the round inner shell 204, target operating pressures, and safety factors. In some embodiments, the end plate thickness $T_{E2}$ of the round inner shell 204 (FIG. 4) may be less than the end plate thickness $T_{E1}$ of the flat inner shell 104 (FIG. 3) for a given material and operating pressure due to the round (e.g., hemispherical) geometry of the end plate portion 228 of the round inner shell 204.

Although the flat inner shell 104 and the round inner shell 204 are shown in FIGS. 3 and 4, respectively, as having a monolithic configuration, the present disclosure is not so limited. For example, the respective flanges 120, 220 may be formed separately from the detector receptacles 124, 224, and the detector receptacles 124, 224 may be coupled to the flanges 120, 220. By way of example and not limitation, the flanges 120, 220 may comprise a stainless steel material, and the detector receptacles 124, 224 may comprise a carbon composite material. In such embodiments, a lower (from the perspective of FIGS. 3 and 4) end of the detector receptacles 124, 224 may be positioned within a groove formed in the respective flanges 120, 220. The detector receptacles 124, 224 may be held in place within the groove by mechanical interference, by an adhesive, by a connector (e.g., a bolt or pin), or by the pressure between the inner shells 104, 204 and the respective outer shells 102, 202.

Figure 5:
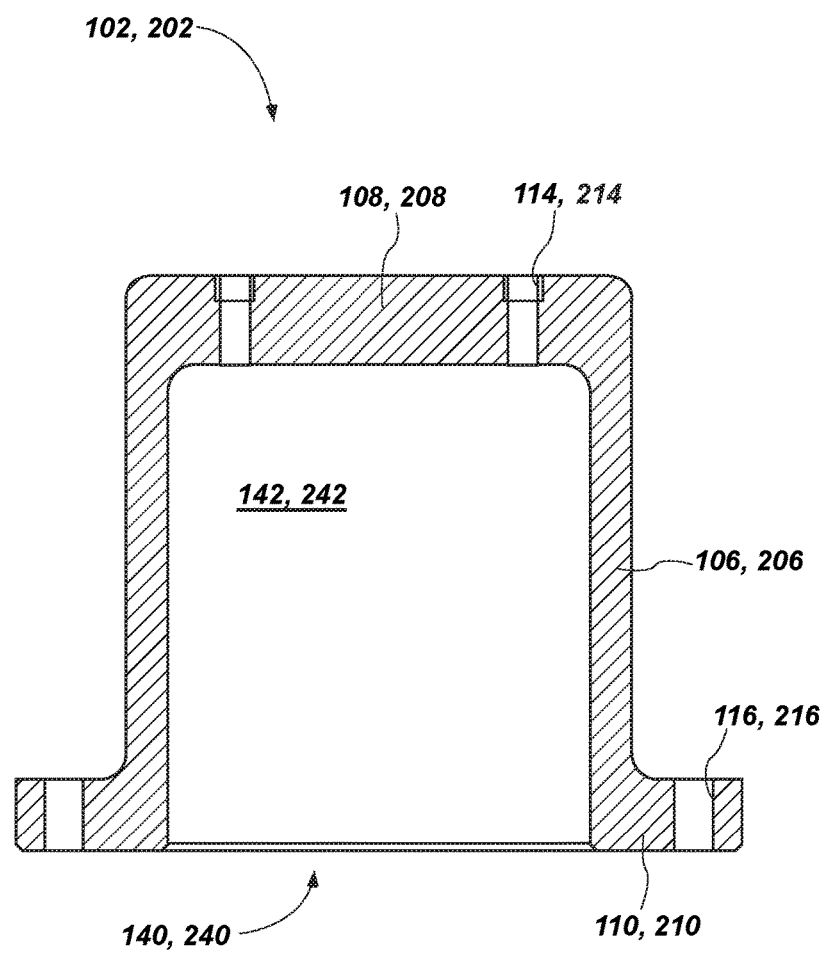
FIG. 5 shows a detailed cross-sectional view of an outer shell of FIG. 1 or FIG. 2.

Referring to FIG. 5, a detailed cross-sectional view of the outer shell 102, 202 of FIGS. 1 and 2 is shown. The outer shell 102, 202 may include an opening 140, 240 into an interior 142, 242 of the outer shell 102, 202. The interior 142, 242 of the outer shell 102, 202 may be defined as a space within and between the cylindrical outer wall portion 106, 206 and the end plate portion 108, 208. The opening 140, 240 may pass through the flange 110, 210 from an end of the outer shell 102, 202 opposite the end plate portion 108, 208. The opening 140, 240 may be sufficiently large to enable the respective detector receptacles 124, 224 of the flat inner shell 104 and/or of the round inner shell 204 to be inserted and positioned at least partially within the interior 142, 242 of the outer shell 102, 202 when in use (see also FIGS. 6 and 7, discussed below).

As discussed above, the outer shell 102, 202 may be formed of any non-reactive material and at any thickness to withstand an operating pressure within the Marinelli-type container 100, 200 (FIGS. 1 and 2) (e.g., at least about 1000 psi, at least about 3000 psi, at least about 5000 psi). For example, the outer shell 102, 202 may be formed of a stainless steel material, an aluminum material, or a carbon composite material. Since, in operation, the outer shell 102, 202 is not positioned between a fluid sample and a radiation detector, the particular material and thickness for the outer shell 102, 202 may be selected without regard to reducing attenuation of a gamma signal from the fluid sample. Rather, in some embodiments, the outer shell 102, 202 may be formed of a material and at a thickness to increase attenuation, to reduce gamma radiation exterior to the outer shell 102, 202, such as to shield personnel and equipment proximate to the outer shell 102, 202 from gamma radiation. By way of example and not limitation, in an embodiment in which the outer shell 102, 202 is formed of a stainless steel material, the end plate portion 108, 208 may have a thickness of between about 1.0 inch and about 2.0 inches, such as about 1.25 inches, and the cylindrical outer wall portion 106, 206 may have a thickness of between about 0.5 inch and about 1.0 inch, such as about 0.6 inch. The actual thicknesses of the end plate portion 108, 208 and of the cylindrical outer wall portion 106, 206 for a given embodiment may depend on various factors, such as the particular material selected for the outer shell 102, 202, the overall size of the outer shell 102, 202, target operating pressures, and safety factors.

Figure 6:
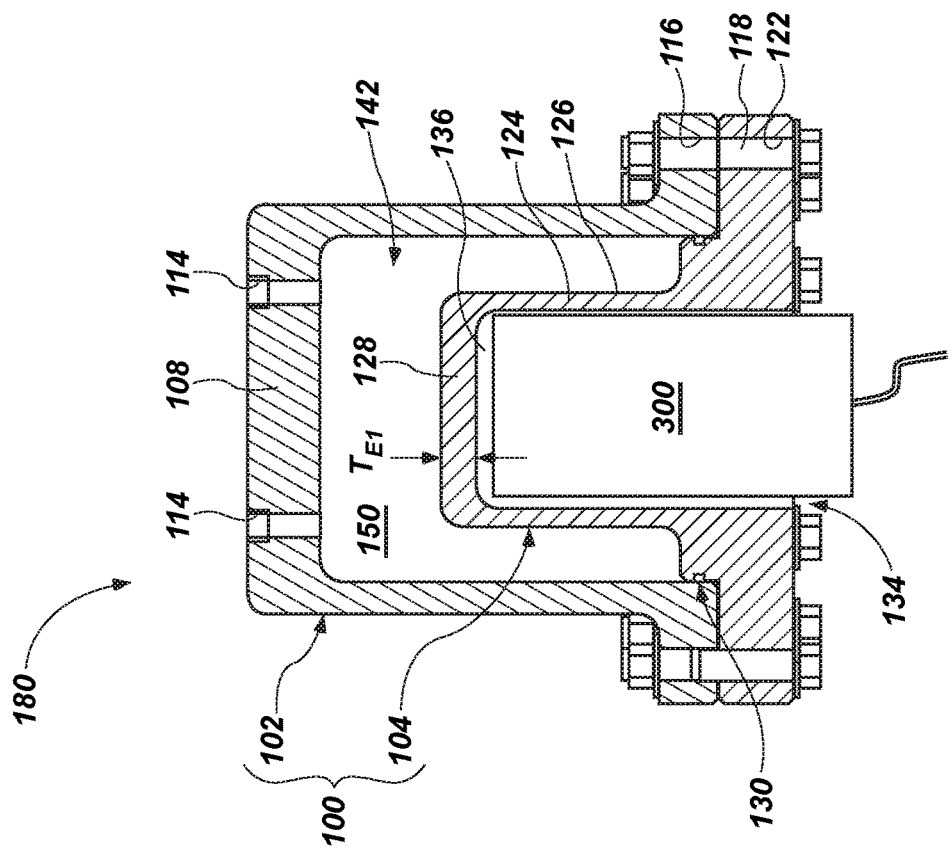
FIG. 6 shows a cross-sectional view of a system for measuring radioactivity in a fluid sample that includes the Marinelli-type container of FIG. 1 and a radiation detector.

Referring to FIG. 6, a system 180 for measuring radioactivity in a fluid (e.g., gas) sample includes the Marinelli-type container 100 of FIG. 1 and a radiation detector 300 positioned at least partially within the interior 136 of the detector receptacle 124 through the opening 134 of the flat inner shell 104. The radiation detector 300 may be any suitable detector known in the art, such as an HPGe radiation detector. A fluid sample space 150 may be defined within the interior 142 of the outer shell 102 between the cylindrical outer wall portion 106 and end plate portion 108 of the outer shell 102 and the cylindrical inner wall portion 126 and end plate portion 128 of the flat inner shell 104. In operation, the fluid sample space 150 may be filled with a compressed or non-compressed fluid sample (e.g., a sample of air including radioxenon) through one of the one or more ports 114 at an operating pressure sufficient to increase a concentration of a radionuclide within the fluid sample space 150 for increased radioactivity that may be more readily sensed and measured by the radiation detector 300 compared to a non-pressurized fluid sample, which would exhibit a relatively reduced concentration of the radionuclide within the fluid sample space 150. Pre-existing fluid (e.g., air) within the fluid sample space 150 may be removed through another of the one or more ports 114, each port 114 being equipped with a fitting and conduit (not shown), which may be configured to permit selective evacuation of the fluid sample space 150, introduction of a fluid sample, and removal of the fluid sample from the fluid sample space 150. A gamma signal (i.e., gamma radiation) may pass from the fluid sample space 150 and through the cylindrical inner wall portion 126 and end plate portion 128 of the detector receptacle 124 to reach the radiation detector 300. As discussed above, the gamma signal may be attenuated by the cylindrical inner wall portion 126 and end plate portion 128 of the detector receptacle 124, but the attenuation may be less than the gain in signal resulting from pressurizing the fluid sample within the fluid sample space 150.

Figure 7:
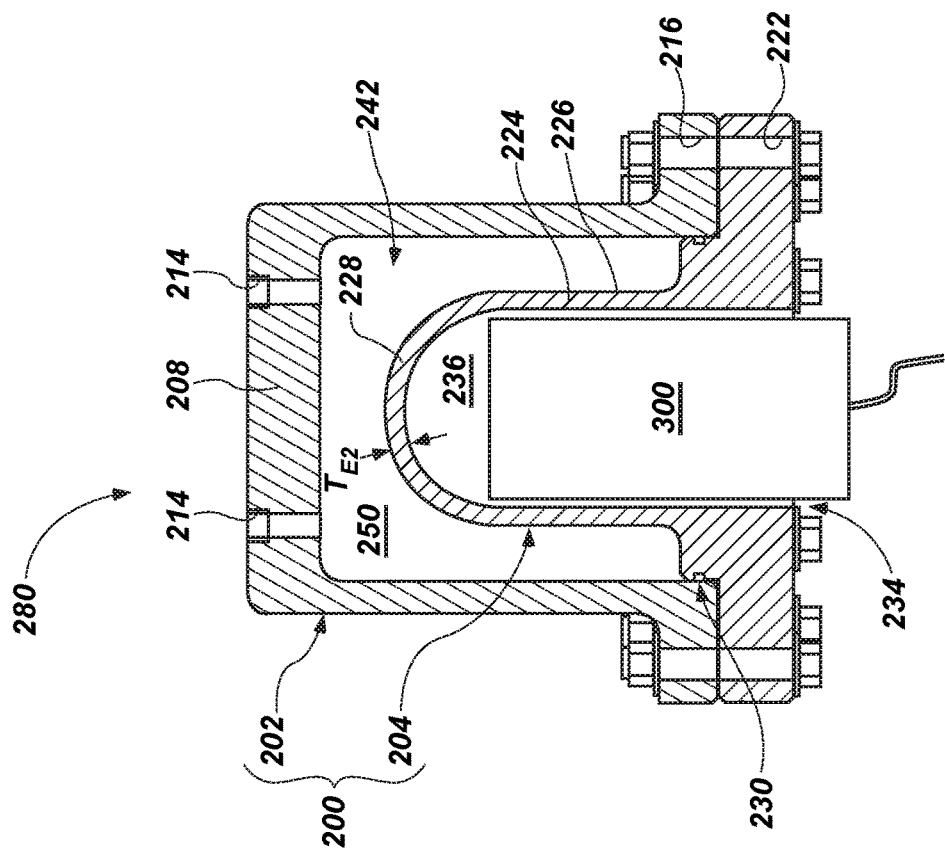
FIG. 7 shows a cross-sectional view of a system for measuring radioactivity in a fluid sample that includes the Marinelli-type container of FIG. 2 and a radiation detector.

Referring to FIG. 7, a system 280 for measuring radioactivity in a fluid (e.g., gas) sample includes the Marinelli-type container 200 of FIG. 2 and a radiation detector 300 positioned at least partially within the interior 236 of the detector receptacle 224 through the opening 234 of the round inner shell 204. A fluid sample space 250 may be defined within the interior 242 of the outer shell 202 between the cylindrical outer wall portion 206 and end plate portion 208 of the outer shell 202 and the cylindrical inner wall portion 226 and end plate portion 228 of the round inner shell 204. In operation, the fluid sample space 250 may be filled with a compressed or non-compressed fluid sample (e.g., a sample of air including radioxenon) through one of the one or more ports 214 at an operating pressure sufficient to increase a concentration of a radionuclide within the fluid sample space 250 for increased radioactivity that may be more readily sensed and measured by the radiation detector 300 compared to a non-pressurized fluid sample, which would exhibit a relatively reduced concentration of the radionuclide within the fluid sample space 250. Pre-existing fluid (e.g., air) within the fluid sample space 250 may be removed through another of the one or more ports 214, each port 214 being equipped with a fitting and conduit (not shown), which may be configured to permit selective evacuation of the fluid sample space 250, introduction of a fluid sample, and removal of the fluid sample from the fluid sample space 250. A gamma signal (i.e., gamma radiation) may pass from the fluid sample space 250 and through the cylindrical inner wall portion 226 and end plate portion 228 of the detector receptacle 224 to reach the radiation detector 300. As discussed above, the gamma signal may be attenuated by the cylindrical inner wall portion 226 and end plate portion 228 of the detector receptacle 224, but the attenuation may be less than the gain in signal resulting from pressurizing the fluid sample within the fluid sample space 250.

Referring to FIG. 7 in conjunction with FIG. 6, the end plate thickness $T_{E2}$ of the round inner shell 204 may be less than the end plate thickness $T_{E1}$ of the flat inner shell 104. The relatively thinner end plate portion 228 of the round inner shell 204 may attenuate a gamma signal through the end plate portion 228 less than through the relatively thicker end plate portion 128 of the flat inner shell 104. However, the geometry of the end plate portion 228 of the round inner shell 204 may hold a portion of the fluid sample farther from the radiation detector 300, while a portion of the fluid sample proximate the flat inner shell 104 may be closer to the corresponding radiation detector 300. Accordingly, the selection of a flat inner shell 104 or a round inner shell 204 for a particular application may be made by one of ordinary skill in the art depending on factors such as operating pressures, cost of manufacture, material of the inner shell 104, 204, the particular radionuclide of interest, the geometry of the radiation detector 300, etc.

The inventors have discovered through testing and modeling that detection and measurement of radiation from radioxenon in air may be improved in pressurized gas samples compared to non-pressurized gas samples using a system similar to the system 180 shown in FIG. 6 or the system 280 shown in FIG. 7. As discussed above, an increase in operating pressure may strengthen the gamma signal from the fluid sample, but may conversely require an increase in thickness of the detector receptacle 124, 224 which, in turn, may result in increased attenuation of the gamma signal. However, the gain in gamma signal may overcome the attenuation loss from the greater thicknesses to provide a more easily measurable signal at the radiation detector 300. For aluminum inner shells 104, 204, it was estimated that about 1000 psi is a sufficient and balanced operating pressure for measuring radiation from $^{133}$Xe in air for both the flat inner shell 104 and the round inner shell 204. For aluminum inner shells 104, 204, it was estimated that between about 1000 psi and about 2000 psi is a sufficient and balanced operating pressure for measuring radiation from $^{135}$Xe in air for both the flat inner shell 104 and the round inner shell 204. For carbon composite inner shells 104, 204, it was estimated that about 3000 psi is a sufficient and balanced operating pressure for measuring radiation from $^{133}$Xe in air for both the flat inner shell 104 and the round inner shell 204. For carbon composite inner shells 104, 204, it was estimated that about 5000 psi is a sufficient and balanced operating pressure for measuring radiation from $^{135}$Xe in air for both the flat inner shell 104 and the round inner shell 204.

The embodiments of the disclosure described above and illustrated in the accompanying drawing figures do not limit the scope of the invention, since these embodiments are merely examples of embodiments of the disclosure. The invention is encompassed by the appended claims and their legal equivalents. Any equivalent embodiments lie within the scope of this disclosure. Indeed, various modifications of the present disclosure, in addition to those shown and described herein, such as other combinations and modifications of the elements described, will become apparent to those of ordinary skill in the art from the description. Such embodiments, combinations, and modifications also fall within the scope of the appended claims and their legal equivalents.

What is claimed is:

1. A container for a fluid sample containing a radionuclide for measurement of radiation from the radionuclide, comprising:
    an outer shell comprising one or more ports extending between an interior and an exterior of the outer shell; and
    an inner shell secured to the outer shell and comprising a detector receptacle sized for at least partial insertion into the interior of the outer shell, the inner shell and the outer shell together at least partially defining a fluid sample space proximate the detector receptacle,
    wherein the outer shell and inner shell are each configured for maintaining an operating pressure within the fluid sample space of at least about 1000 psi.

2. The container of claim 1, wherein the outer shell and inner shell are each configured for maintaining an operating pressure within the fluid sample space of at least about 2000 psi during operation.

3. The container of claim 1, wherein the outer shell comprises a first flange and wherein the inner shell comprises a second flange for coupling the outer shell to the inner shell.

4. The container of claim 3, wherein first holes extend through the first flange and second holes extend through the second flange, the first holes and second holes configured for receipt of bolts for coupling the outer shell to the inner shell.

5. The container of claim 1, wherein the outer shell comprises a material selected from the group consisting of a stainless steel material, an aluminum material, and a carbon composite material.

6. The container of claim 5, wherein the outer shell comprises a stainless steel material.

7. The container of claim 1, wherein the inner shell comprises a material selected from the group consisting of an aluminum material and a carbon composite material.

8. The container of claim 1, wherein the inner shell comprises a cylindrical wall portion and an end plate portion.

9. The container of claim 8, wherein the end plate portion is substantially flat.

10. The container of claim 9, wherein the end plate portion has an end plate thickness that is greater than a wall thickness of the cylindrical wall portion.

11. The container of claim 8, wherein the end plate portion is rounded.

12. The container of claim 11, wherein the rounded end plate portion is hemispherical.

13. The container of claim 11, wherein the rounded end plate portion has an end plate thickness that is substantially the same as a wall thickness of the cylindrical wall portion.

14. The container of claim 1, further comprising an O-ring between the outer shell and the inner shell providing a fluid-tight seal between the outer shell and the inner shell.

15. A system for measuring radioactivity in a fluid, the system comprising:
 a container as claimed in any one of claims 1 through 14; and
 a radiation detector received at least partially within an interior of the detector receptacle.

16. The system of claim 15, wherein the radiation detector comprises a high-purity germanium detector.

17. A method of measuring radioactivity in a fluid sample, the method comprising:
 introducing the fluid sample into a Marinelli-type container;
 maintaining a pressure of the fluid sample within the Marinelli-type container at least at about 1000 psi;
 positioning a radiation detector within an inner shell of the Marinelli-type container; and
 measuring a gamma signal from the fluid sample within the Marinelli-type container.

18. The method of claim 17, wherein introducing the fluid sample into a Marinelli-type container comprises introducing radioxenon in air into the Marinelli-type container.

19. The method of claim 17, wherein maintaining a pressure of the fluid sample within the Marinelli-type container comprises maintaining a pressure of at least about 2000 psi.

20. The method of claim 17, wherein maintaining a pressure of the fluid sample within the Marinelli-type container comprises maintaining a pressure of at least about 3000 psi.

21. The method of claim 17, wherein positioning a radiation detector within an inner shell of the Marinelli-type container comprises positioning the radiation detector within an inner shell comprising a material selected from the group of an aluminum material and a carbon composite material.

\* \* \* \* \*

UNITED STATES PATENT AND TRADEMARK OFFICE
CERTIFICATE OF CORRECTION

PATENT NO. : 9,683,976 B2
APPLICATION NO. : 14/826056
DATED : June 20, 2017
INVENTOR(S) : Nicholas R. Mann et al.

It is certified that error appears in the above-identified patent and that said Letters Patent is hereby corrected as shown below:

In the Specification
Column 3, Line 53, change "a high purity gel" to --a high purity germanium--

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*